United States Patent [19]

Friedman et al.

[11] Patent Number: 5,023,183

[45] Date of Patent: Jun. 11, 1991

[54] MASS PRODUCTION IN LIQUID CULTURE OF INSECT-KILLING NEMATODES

[75] Inventors: Milton J. Friedman, San Francisco; Susan E. Langston, Saratoga; Sonia Pollitt, San Bruno, all of Calif.

[73] Assignee: Biosys Corporation, Palo Alto, Calif.

[21] Appl. No.: 123,130

[22] Filed: Nov. 20, 1987

[51] Int. Cl.$^5$ .................. A01K 45/00; A01K 67/033; C12N 5/00

[52] U.S. Cl. .................. 435/240.3; 119/6.7; 800/2

[58] Field of Search .............. 435/240.3; 119/1; 800/1, 2

[56] References Cited

U.S. PATENT DOCUMENTS 3,926,737 12/1975 Wilson et al. .................. 195/108
4,454,227 6/1984 Röder .................. 435/240

FOREIGN PATENT DOCUMENTS

86/01074 2/1986 PCT Int'l Appl. .

OTHER PUBLICATIONS

Bedding, *Ann. Appl. Biol.*, (1984), 104:117–120.
Stoll, N., (1961), *J. Helminthol.*, Lister Suppl., pp. 169–174.
Jackson, G. J., (1973), *Exp. Parasitol.*, 34:111–114.
Beucher, E. J., et al., (1970), *Nematologia*, 16:403–409.
Beucher et al., (1971), *J. Nematol.*, 3:199–200.
Wouts, W. M., et al., (1981), *J. Nematol.*, 13:4670469.
A. Roder, (1982), *Naturwissenschaften*, 69:92–93.
M. S. Schnier and B. Fried, (1980), *Int. J. Parasitol.*, 10:391–395.
P. F. Basch et al., (1973), *J. Parasitol.*, 59:319–322.
D. W. W. Kannangara, (1974), *Int. J. Parasitol.*, 4:675–676.
Jackson et al., *J. Parasitology*, (1965), 51(5):727–730.

Primary Examiner—Elizabeth C. Weimar
Assistant Examiner—Christopher Low
Attorney, Agent, or Firm—Irell & Manella

[57] ABSTRACT

Entomogenous nematodes can be used as biological insecticides for the control of certain pests. The present invention provides a large-scale production in liquid culture of these entomogenous nematodes using an improved liquid culture medium. The medium uses an emulsifier to provide a well homogenized growth medium. The invention also provides a method of cultivating entomogenous nematodes on a commercial scale, in liquid culture, in fermenters by controlling the agitation rate as a function of oxygen demand.

16 Claims, 1 Drawing Sheet

MASS PRODUCTION IN LIQUID CULTURE OF INSECT-KILLING NEMATODES

TECHNICAL FIELD

The invention relates to insect control employing biological agents especially for the benefit of agriculture, garden and household insects. In particular, it relates to large-scale production in liquid culture of insect parasitic nematodes using an improved nutrient medium and optimal culturing conditions.

BACKGROUND ART

Nematodes represent a group of unsegmented round worms. They are simple in anatomy, having a simple gut and elongated fusiform shape. They are divided into numerous Families, some of which are free living while others are parasitic to plants or animals. Those which are parasitic to insects are called entomogenous or entomopathogenic nematodes.

The Order of greatest commercial interest for insect control is the Order Rhabditida, which contains several Families, many of whose members are parasitic to insects. Prominent among these Families are the Steinernematids and Heterorhabditids. A general discussion of the classification of nematodes, and the entomogenous Families thereof is found in Poinar, G. O. "The Natural History of Nematodes" (1983), Prentice-Hall, Inc., N.J.

Nematodes have a standard life cycle comprising five stages which are delineated by a molting process in which a new cuticle is formed and the old one shed. Briefly, the adults of stage 5 reproduce, and the eggs generate stage 1 larvae, which, under appropriate conditions, transit to stage 2. Normally, the stage 2 larvae simply develop to stage 3 larvae and thence to stage 4 larvae, which then complete the cycle to the adult stage. However, and of interest to the use of nematodes for insect control, when conditions are relatively unfavorable for continuing growth and reproduction, the stage 2 larvae of Steinernematid and Heterorhabditid nematodes develop instead into "stage 3 infective juveniles" or "IJs". Under these conditions, the cuticle characteristic of the second stage is retained and is called the sheath. It completely encloses the nematode. IJs are infective to insects and complete their life cycle through stage 4 and adult at the expense of the host.

Steinernematid and Heterorhabditid IJ nematodes are an effective means of insect control. They are identifiable morphologically and normally live in surface water films around soil particles. They require oxygen and moisture for survival, but do not feed; they utilize their own food reserves as an energy source. They remain infective if the sheath is removed.

One other aspect of Steinernematid and Heterorhabditid nematode biology is significant: nematodes within these families are symbiotic with species of bacteria which are primarily but not totally responsible for their entomopathogenic properties. Growth of nematodes is favored in the presence of an associated symbiont, presumably because the symbiont serves as an easily assimilated food source.

The monoxenic culture method of Bedding [(1984) *Ann Appl Biol* 104:117-120] has been proposed for the mass production of entomogenous nematodes. The Bedding method uses a solid phase matrix of plastic foam impregnated with homogenized animal tissue in which the nematodes are grown. The technique provides a well-aerated substrate for the growth of both the bacterial symbiont and the nematode. The Bedding process has been applied to the production of $10^9$ nematodes in a batch, but potential markets may require a production capacity 10,000 times this amount. A scaled up version of the Bedding process would require expensive automated equipment, would be difficult to maintain in an aseptic state, and would present difficulties in medium preparation and nematode harvesting. A liquid, monoxenic process would avoid these limitations.

Liquid, monoxenic cultures of entomogenous nematodes are usually grown in small drops of insect hemolymph. Axenic liquid cultures have been reported but are limited in efficiency and require expensive nutritional additives. For example, in the course of nutritional studies, liquid culture volumes of less than 100 ml were used by Stoll, N. (1961) *J Helminthol*, Lister Suppl, pp. 169-174; Jackson, G. J. (1973) *Exp Parasitol* 34:111-114; Hansen, E., et al (1967), 42nd Ann Meeting Am Soc Parasitol; Lower, W. M. R., et al (1970) *Nematologia* 16:563-566;,and Beucher, E. J., et al (1970) *Nematologia* 16:403-409. Nevertheless, these reports demonstrate that the biological and physiological requirements of the nematodes can be met in liquid suspension. Some means for aeration of these cultures is required and may be supplied by either diffusion into thin liquid layers, shaking, or bubbling.

One of the greater difficulties in developing a liquid, monoxenic culture is in providing sufficient aeration for both the bacteria and the nematodes without exposing the nematodes to excessive shear forces. One technique has been reported for the growth of *C. elegans*, a free-living nematode, in liquid, monoxenic culture. In this technique, bacteria are suspended with nematodes in a non-nutrient salt solution. Under these conditions, the bacteria have little free nutrient to metabolize and therefore have a low oxygen demand. During studies leading to the present invention, it was found that this same technique could be used for the culture of *N. carpocapsae* as long as a sterol additive was provided. The bacterial requirement was found to be so high, however, that commercial exploitation of the technique was economically precluded.

PCT Patent Application No. 86/01074, published Feb. 27, 1986 (hereinafter referred to as "Pace et al"), described a process for large-scale culture of nematodes which addresses some of the problems associated with aeration requirements. This procedure determined the stirring rate in a stirred reactor at which adult nematodes are disrupted. The stirring rate was then set at a level below this determined rate and maintained throughout the culture period.

Pace et al also describe the use of a conventional liquid culture medium composed of ox kidney homogenate and yeast extract. Other media for nematode culture have included soy peptone-yeast extract-dextrose (Buecher et al (1971) *J Nematol* 3:199-200 for use in axenic liquid culture); peptone-glucose and bacteria (Dutky, S. R., et al (1967) *J Nematol* 13:140 for monoxenic culture on agar); and nutrient broth-yeast extract-soy flour-corn oil (Wouts, W. M., et al (1981) *J Nematol* 13:467-469, for monoxenic solid support or foam). Each of these media contain one or more ingredients that is expensive or difficult to prepare.

The monoxenic liquid culture method of Pace et al gave a reproductive rate in the first 10 days of 20 (an increase from 2,000 to 40,000 nematodes per milliliter) and reported the formation of infective juveniles in liquid culture after 20 days. Other investigators using axenic systems have reported similar reproductive rates, but did not report observing significant levels of infectious juveniles.

It has been discovered that a critical component in a liquid, nutrient culture medium supportive of monoxenic nematode culture but controlled for oxygen demand, is the requirement of an emulsifier, such as egg yolk, which serves to facilitate the utilization of added oils or fats. To date, there have not been any reports using an emulsifier to benefit liquid culture of entomogenous nematodes; however, egg yolk has been used as a replacement for animal serum in the culture of mammalian parasites and has met with both success and failure.

A. Roder [(1982) *Naturwissenschaften* 69:92–93] used egg yolk to replace fetal calf serum in the culture of insect cells. M. S. Schnier and B. Fried [(1981) *Int J Parasitol* 10:391–395] used egg yolk in NCTC 135 in the culture of *Ablosoma suwaense*, a parasitic trematode (a worm in the fluke phylum). In addition, egg yolk has frequently been used in bacterial cell cultures especially with Staphylococcus. P. F. Busch et al [(1973) *J Parasitol* 59:319–322] found that egg yolk did not benefit Cotylurus (a trematode) culture and D. W. W. Kannangara [(1974) *Int J Parasitol* 4:675–6] found that egg yolk did not benefit Paragonimus culture. None of these cases involved a role for egg yolk in emulsifying an oil component.

It is, therefore, an object of the present invention to improve.. the production efficiency of entomogenous nematodes in liquid culture.

It is a further object of the invention to provide an improved liquid culture medium support of monoxenic nematode culture but controlled for oxygen demand. This nutrient medium is easily prepared and is relatively inexpensive to produce as compared to presently available media.

Yet a further object of the invention provides a method to enhance bacterial and nematode development wherein the agitation rate is varied depending on the changing oxygen transfer requirements associated with each nematode developmental stage.

DISCLOSURE OF THE INVENTION

The present invention provides a commercially inexpensive medium for culturing entomogenous nematodes in liquid culture wherein the essential nutrients are an emulsifier, such as egg yolk, a yeast source, vegetable oil, and a source of protein. A preferred embodiment of the invention comprises about 1–2% egg yolk, about 0.1–1.0% (dry weight) yeast cells, about 2–5% corn oil, and about 1–3% soy flour.

The invention also provides a method for culturing entomogenous nematodes in the liquid medium described above, wherein the medium is preincubated with a bacterial symbiont, a culture of entomogenous nematodes is then used to inoculate this medium, and means for agitating the inoculated medium during the nematode reproductive cycle are provided. This method supports a higher reproduction rate and gives rise to infectious nematodes after ten to sixteen days.

Also provided is a method of culturing entomogenous nematodes for producing high concentrations of relatively pure infective stage nematodes in a fermentation vessel, which comprises varying the agitation rate according to the changes in oxygen transfer requirements to differentially provide optimal conditions for nematode reproduction and growth.

MODES FOR CARRYING OUT THE INVENTION

A. Definitions

Figure 1:
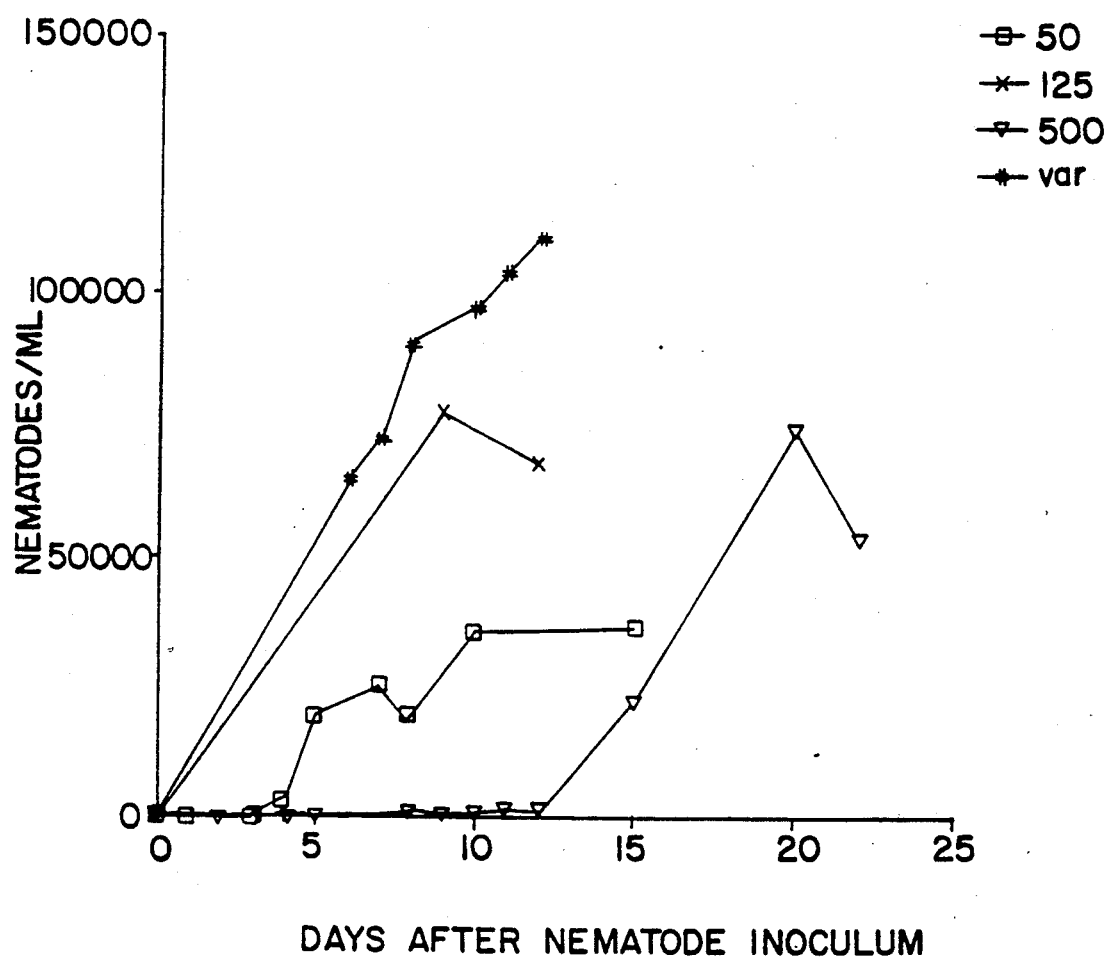
FIG. 1 is an illustration of the relationship between agitation levels and nematode reproduction during the fermentation cycle of entomogenous nematodes. The stirring rate was either constant at 50 rpm (designated by the open squares), 125 rpm (designated by the X's), or 500 rpm (designated by the inverted triangles), or was varied (designated by the "#'s") during the course of the run to maintain a level of 64 mm Hg oxygen transfer.

"Entomogenous nematodes" refers to nematodes which are parasitic to one or more species of insect. The most important Order of entomogenous nematodes is the Rhabditida, and the invention is directed chiefly to the cultivation and/or shipment of two Rhabditid families in this group: the Steinernematidae and the Heterorhabditidae. However, other entomogenous families may also be suitable as subjects to which the methods of the invention may be applied, and include Diplogasteridae, Panagrolaimidae, Rhabditidae, and Syrophonematidae, together with non-Rhabditid families including the Allantonematidae, Aphelenchoididae, Entaphelenchidae, Mermithidae, Neotylenchidae, Sphaerulariidae, and Tetradonematidae.

As set forth above, for the Rhabditida, the most important families for commercial use are the Steinernematidae and the Heterorhabditidae. References in the literature to "Neoaplectana" refer to a particular Genus of the Steinernematidae, and the terms Neoaplectana and Steinernema as designators for specific species— e.g., *N.glaseri* or *S.glaseri*—are sometimes used interchangeably.

While the classification of the various groups of nematodes may be confusing, it is clear that the invention is directed to those genera which have the characteristics of being infective to insects, and which have as a stage in their life cycles, stage 3 infective juveniles (IJs) with the characteristics described in the background section above. Depending on the agricultural application intended, i.e., the insect targeted, one or more of the species may be particularly advantageous.

"Infective juvenile" or "IJ" refers to a nonadult stage capable of invading and infecting an insect host. For the families which are the subject of the present invention, these are stage 3 IJs.

"Agitation" refers to any physical means to introduce flow movement in the fermentation vessel including, but not limited to, mechanical paddle stirring and bubbling of forced air.

B. General Description

The infective juveniles which are the subjects of the procedures herein are useful in controlling a variety of insect pests, including borers, root weevils, caterpillars, beetle grubs, corn root worms, Japanese beetles, and mole crickets. Major agricultural products which are targeted by such infective juveniles include corn, strawberries, almonds, greenhouse crops, mushrooms, sugar cane, and potatoes. Poultry raising facilities and other animal housing, also, are kept free of flies. In a typical agricultural application, infective juveniles are applied to the target environment in large numbers. For example, for control of sciarid flies in mushroom houses, approximately $5 \times 10^9$ worms are applied in each house.

The present invention encompasses methods for the large-scale liquid culture of entomopathogenic nematodes using an improved liquid culture medium. The medium comprises an emulsifier, a yeast source, vegetable oil, a source of protein, and may optionally contain additional components such as salts, antifoams, nutrients and buffers. It has been found that the oil component, in the presence of an emulsifier such as egg yolk, is well emulsified and remains well emulsified for several days of fermentation. This is an marked contrast with formulations without egg yolk in which the oil separates and rises to the top of the fermentation vehicle. Egg yolk is preferred as the emulsifier and, to date, no upper limit for the emulsifier concentration in the medium has been determined. It has been found that a 1-2% volume/volume is quite operable. While egg yolk is a preferred emulsifier, lecithin can be substituted in part for the egg yolk component. Generally, 0.1-0.5% of lecithin can be used in conjunction with egg yolk. Other emulsifiers include glycerol monostearate or monooleate, polyoxyethylenesorbitan and fatty acid-carbohydrate esters.

The medium should also include a yeast source, such as yeast extract and yeast cells. Yeast cells are preferred as a less expensive alternative to the use of yeast extracts. It is preferred to use about 0.1 to 1.0% (dry weight) or a comparable 0.3 to 3% (wet weight) of the yeast source in the culture medium.

A variety of vegetable oils are available for use in the present invention, including, but not limited to, corn, safflower, soy, sunflower, and rapeseed. A preferred source of vegetable oil for use in the medium is corn oil with a concentration of 2 to 5% (v/v).

The source of protein also may be provided by a variety of sources. For example, protein extracts including animal- or plant-derived material are well-known components of media cultures. Dried animal organ extracts, such as EnLivPro and meat peptone, fish meal, soy peptone, and soy flour are all available for use in the present invention. Of these sources, soy flour is preferred. While no upper limit for the soy flour concentration has been determined, it is preferable to use about 1 to 3% weight/volume.

While not essential, additional ingredients can be added to the medium if desired. For example, salts, cholesterol, sterile water or phosphate-buffered saline have been utilized in the present invention and will not compromise the yield of resulting infectious nematodes.

A preferred liquid culture medium for mass production of entomogenous nematodes thus comprises about 1-2% yeast cells, about 2-5% corn oil, and about 1-3% soy flour. This preferred medium is prepared from ingredients that are unprocessed raw materials used in the food industry and are readily available.

The medium is prepared by first mixing the vegetable oil and the egg yolk and then homogenizing this oily material with water. Next, the remaining ingredients are added and the medium is sterilized by autoclaving. While the performance of the initial mixing step is not mandatory, it has been found that media prepared in this manner forms a more stable emulsion and produces higher yields of infectious nematodes.

In another embodiment, the invention encompasses a method for the large-scale liquid culture of ettomogenous nematodes for producing high concentrations of infectious nematodes, whereby the culture medium of the present invention is preinoculated with the nematodes' symbiotic bacteria. As is recognized in the art, it is preferable to use a population of bacteria in their primary form. The addition of the symbiotic bacteria is important to maximize the yield of the process and the infectivity of nematodes against insects.

Approximately $1 \times 10^7$ bacterial cells per milliliter of medium is grown for approximately 24-48 hours at 25°-30° C. prior to inoculation with a nematode culture. After bacterial inoculation into the medium, the air flow rate is introduced at approximately 1 fermenter volume/minute, and the stirring rate is adjusted to control dissolved oxygen at the level of 50% saturation although other conditions can be used to deliver sufficient oxygen to the culture.

The juvenile nematodes can be either infectious nematodes or J1 through J4 stage juveniles with J3s being the preferred form. The nematode inoculate concentration can vary between 100 and 5,000 nematodes per milliliter of medium. At the time of nematode inoculation, the pressure can be adjusted to up to 3 bars if desired to increase oxygen availability. As the nematode adult stage of the fermentation is reached, the oxygen demand of the bacteria drops and thus agitation can be decreased.

After inoculation, the temperature is lowered to 20°-28° C., depending on the nematode strain, and maintained at this temperature throughout the growth of the culture.

In a specific embodiment of this method wherein an Erlenmeyer shake flask is utilized, it is preferred to maintain the volume of the fermentation culture at a 1:4-1:8 ratio with the flask volume. The culture is shaken at 150 rpm on a rotary shaker throughout the culture period of 10 to 16 days.

A stirred tank reactor is a preferred fermentation vessel, notwithstanding the high shear conditions created within such vessels. When an air flow rate of approximately 1 fermenter volume/minute is maintained during a fermentation, the stirring rate can be adjusted to fairly high levels to accommodate changes in oxygen demand at any particular growth stage of the culture without detrimental effect on the resultant yield of infectious juveniles. As described below in greater detail, the shear sensitivity of the culture has been determined for the various growth stages and attendant oxygen demands of the fermentation cultures and thus the upper parameters of the rate of agitation have been evaluated.

The concentration of second generation juveniles was determined beginning at day 8 through day 16 of the fermentation period. The medium was found to support higher levels of reproduction than other media, exceeding a 200-fold increase per generation, and provide infectious juveniles in a shorter period, e.g., within 10 to 16 days, than other reported methods. Thus, the medium and method of the present invention provides a process whereby large-scale entomogenous nematodes can easily be cultivated using inexpensive, readily available ingredients.

While a batch manufacturing process has been described above, the invention also provides for a "fed batch" process wherein medium is resupplied during the J3 and J4 development stage. This method provides an additional source of nutrients for the fermentation culture and may overcome any nutrient-limiting growth condition.

A further embodiment of the invention relates to a method for maintaining bacterial and nematode development in mixed vessels wherein the agitation rate is varied according to the changing oxygen transfer requirements to differentially provide optimal conditions for nematode reproduction and growth. The conditions obtained in mixed vessels are at best difficult to predict but are critical to successful nematode production. The critical parameters are temperature, dissolved oxygen tension, and shear stress and other means of physical strain. The temperature of the process can easily be optimized in small vessels or static cultures. Maintaining the optimal temperature has not proven difficult in large vessels.

Dissolved oxygen must be maintained over approximately 32 mm Hg throughout most of the process, but must be higher than 40 mm Hg and preferably 80 mm Hg when adults are developing and laying eggs. The difficulty of obtaining these conditions in mixed tanks depends on the oxygen demand of the process and the oxygen transfer rate. The oxygen transfer rate is composed of the air flow rate, the bubble size distribution, and the degree of mixing. The peak oxygen demand during the process described herein is approximately 20 mmol/hr, but, at other times during the fermentation, can be 5 mmol/hr or lower. Maintaining the critical oxygen tension in stirred tank reactors during times of peak oxygen demand can require high speed agitation.

It has long been recognized that intense agitation can inhibit nematode reproduction (Stoll, N. (1953) *J Parasitol* 39:422-444). Pace et al, supra, describe a procedure for determining the stirring rate in a stirred reactor at which adult nematodes are disrupted. They define a "shear force" that can disrupt adult nematodes as the minimum tip speed of the agitator in their reactor at which disruption occurs. It is, however, well recognized that shear stress is the product of shear rate (proportional to tip speed) and viscosity (Bowen, R. L. (1986) *Chem Engineering*, June 9, pp. 55-63). The measurements of Pace et al of allowable tip speeds were performed in water with a viscosity of 1 cP, while the viscosity of the medium in their process was not determined. The method described therefore is unable to predict stress conditions during the process itself, where viscosity is unknown and probably variable. Many means have been published for calculating maximum shear stress, but it is generally recognized that none of these methods can be used reliably to determine allowable shear conditions during scale-up of biological processes (Trilli, A. (1986) *Industrial Microbiology*, American Society of Microbiology, pp. 277-307).

There are, however, two strategies which can be gainfully employed in optimizing the balance between oxygen transfer rate and agitation intensity. One is to use a nonstirred vessel, such as a bubble column or an air-lift reactor, which is known to be associated with low (but finite) shear forces. Another strategy particularly useful with fermentation vessels such as shake flasks and stirred tank reactors, is to limit agitation intensity only during periods when shear forces are indeed limiting and increase agitation intensity only when needed for oxygen transfer. Unlike many fermentation processes, nematode production is characterized by a changing distribution of developmental stages during the process. For example, adult nematodes are predominant between days 2 and 5 after nematode inoculation, while young juveniles predominate from day 6 onwards. The method of the present invention is based on the discovery that the oxygen demand is greatest during the initial growth of bacteria, declines while adults are developing and increases again as juveniles increase in number. In addition, it has been discovered that young juveniles are considerably less sensitive to shear stress than adults. For example, the effects of shear were tested by placing nematodes between a rotating bob and a hollow cylinder where the gap between the two surfaces was 2 mm. The effects of shear were as follows:

| Stage of Nematode | Rpm When Disrupted |
|---|---|
| J1 | 3000 |
| J2-J3 | 2800 |
| Adults | 1800 |

A separate experiment in a laminar shear device failed to disrupt adults at 630 dyne/cm$^2$.

While it is difficult to compare the shear forces found in one vessel with those found in another, it is clear that adults are more sensitive than younger forms. A rough extrapolation from the above results would predict that disruption would occur in a 20l fermenter at about 500 rpm and in a 2500l fermenter at less than 100 rpm. Thus, this knowledge allows control of the fermentation process such that agitation rates are varied to differentially provide optimal conditions to the predominate infectious stage of nematode development in the culture.

After the fermentation is completed, the nematodes are harvested directly from the fermentation vessel. The harvesting can be accomplished using any of a number of conventional procedures to separate the nematodes from the media, including centrifugation, settling and filtration. In the present method, a solid bowl centrifuge was used to separate the nematodes from the viscous part of the medium. The slurry was run through the bowl centrifuge at a maximal flow rate of 6 L/min at approximately 2500-3000 rpm. The slurry was further clarified to separate the nematodes from the dirt, oil and non-IJ elements. Thus, the slurry was diluted with a mild soap, such as Ivory ® soap, at a concentration of 2% (w/v). At this point, a visible change in surface tension is observed. The product is then run through a shear pump to disperse particles. The resulting slurry is recentrifuged at maximal flow and minimal rate of revolution to retain the majority of the IJ's.

The clarification step was repeated until sufficient cleaning was achieved which was determined by microscopic observation of the nematode/particle distribution.

Following product recovery, a concentrating step can be performed if desired.

Notwithstanding other forms which may fall within the broad form of the present invention, the following examples illustrate the growth of different nematode strains, using additional bacterial symbionts. It should be noted that the invention is applicable to all strains of entomogenous nematodes, although the examples illustrate only selected strains.

Thus, the invention will be further described by the following examples. These are provided only to illustrate embodiments of the invention and are not to be construed as limitations on the invention's scope.

EXAMPLE 1

A medium containing 0.5% NaCl, 0.25% KH$_2$PO$_4$, 0.5% egg yolk, 3.0% (wet weight) yeast cells, 1.0% or 2.0% soy flour, 0.5% EnLivPro, 5.0% corn oil, and 20 mg/l cholesterol, pH 8.0, was autoclaved in 30 ml volumes in 125 ml flasks.

The sterile medium was inoculated with $3 \times 10^8$ *Xenorhabdus nemotophilus* bacteria and incubated at 28° C. on a rotary shaker (150 rpm). After approximately 24 hours, *Neoaplectana carpocapsae* (all IJs) were added to densities of 2,000, 1,000, 500, and 200/ml. The temperature of incubation was lowered to 25° C.

Samples were taken 5 and 8 days after nematode inoculation. The following table presents the total nematode population on Day 5 and the infective juvenile population on Day 8.

| Inoculum | Soy % | Day 5 (IJs) | Day 8 (IJs) |
|---|---|---|---|
| 2000 | 1 | 134000 | 80000 |
| 1000 | 1 | 134000 | 74000 |
| 500 | 1 | 118000 | 58000 |
| 200 | 1 | 85000 | 66000 |
| 2000 | 2 | 89000 | 95000 |
| 1000 | 2 | 158000 | 110000 |
| 500 | 2 | 137000 | 102000 |
| 200 | 2 | 141000 | 95000 |

The best reproductive rate was 705. Nematodes harvested from these cultures were pathogenic towards insects.

EXAMPLE 2

Plastic dishes with wells of 1 cm diameter were used for 0.25 ml cultures of *N. carpocapsae*. Medium contained 0.5% NaCl, 0.25% $KH_2PO_4$, 3.0% (wet weight) yeast cells, 2.0% soy flour, 5% corn oil, 0.625% EnLivPro, and variable egg yolk concentration as provided below. Medium inoculated with *X. nematophilus* (quantity) and *N. carpocapsae* (quantity) was incubated at 25° C. After 7 days, the counts were as shown:

| Egg yolk | Nemas/ml |
|---|---|
| 1% | 56,500 |
| 0.25% | 27,000 |
| 0% | 13,000 |

EXAMPLE 3

A medium containing 2.0% soy flour, 1.0% egg yolk, 0.625% dried animal protein (EnLivPro), 0.5% yeast cell (dry wt.), 5% corn oil, 0.5% NaCl, and $KH_2PO_4$, pH 8.0, was autoclaved in 30 ml volumes in four 125 ml Erlenmeyer flasks.

The sterile medium in each flask was inoculated with $3 \times 10^8$ *Xenorhabdis nemotophilus* bacteria and incubated at 28° C. on a rotary shaker (150 rpm). After 72 hours, two of the flasks were independently inoculated with ~1,000 juveniles/ml of either J1-J2 *N. carpocapsae* inoculum or J3-J4 *N. carpocapsae* inoculum. After inoculation with the nematodes, the flasks were incubated at 25° C. with shaking at 150 rpm.

The nematode densities were counted at the end of the experiment of 7 days (168 hours) after nematode inoculation. (The stage of juvenile inoculum is noted below):

| Bacterial incubation | Js | Density at 7 days |
|---|---|---|
| 69 hours | 1-2 | 68,500 ± 6,557 n = 4/2 |
| 68.5 hours | 3-4 | 107,778 ± 10,616 n = 3/3 |

*n = no. of counts/no. of counts per flask.

The use of a juvenile inoculum comprised of J3-J4s (this experiment used an inoculum largely comprised of J3s) is 50% more successful than an inoculum comprised of J1-J2s.

EXAMPLE 4

A glass fermenter 10 cm in diameter × 75 cm high was operated as an air-lift reactor with a draft tube 5 cm in diameter × 20 cm high. A 40 micron porosity sintered metal sparger was positioned at the bottom of the draft tube.

A culture of *N. carpocapsae* was grown as in Example 3, except that the volume was 6 liters. Air was introduced at a rate of 6 liters/minute throughout the experiment. On day 7 a nematode density of 95,000/ml was obtained.

EXAMPLE 5

A 20 liter stirred tank fermenter (Bioengineering) containing 16 liters of medium, was inoculated with *X. nematophilus* and, after 48 hrs, *N. carpocapsae*. The fermenter was operated with an air-flow of 16 liters/minute through a ring sparger. The fermenter was stirred at 250 rpm until the dissolved oxygen (DO) fell below 64 mm Hg. At that time, the rpm was increased to 300 rpm and was increased by 50 or 100 rpm whenever the DO dropped below 64 mm Hg until a peak rpm of 500 was reached. When the DO rose above 96 mm Hg, the rpm was decreased by 50 or 100 rpm increments to a final speed of 250 rpm.

Referring now to FIG. 1 of the accompanying drawings, the results illustrate the effect various stirring rates have on the reproductive capacity of cultured nematodes. The stirring rates were set at 50 rpm (depicted by the open squares), 125 rpm (depicted by the "X's"), or 500 rpm (depicted by the inverted triangles) or was varied (depicted by the "*'s") during the course of the run to maintain 64 mm Hg oxygen tension.

The oxygen tension in both the 50 and the 125 rpm runs decreased to 0 mm Hg during the period between 5 and 12 days after nematode inoculation. The oxygen tension was successfully maintained above 64 mm Hg in both the 500 rpm run and the variable control run.

Utility

Entomogenous nematodes produced by the method of the invention may be used as broad spectrum biological insecticides.

The nematodes may be administered by known methods such as spraying on crops, injecting into tree trunks, spraying on soil, and applying to soil in solid form such as pellets, in diluted or undiluted form.

We claim:

1. An emulsified liquid medium inoculated with bacteria for culturing entomogenous nematodes in liquid culture, said medium comprising an emulsifier, a yeast source, vegetable oil, and a source of protein,
    wherein said medium has been sterilized prior to inoculation with bacteria symbiotic with said nematodes.

2. The medium of claim 1 wherein the emulsifier is provided by egg yolk.

3. The medium of claim 1 wherein the yeast source is provided by yeast cells.

4. The medium of claim 1 wherein the vegetable oil is corn oil.

5. The medium of claim 1 wherein the source of protein is soy flour.

6. The medium of claim 1 which comprises about 1-2% egg yolk, about 0.1-0.5% yeast cells, about 2-5% corn oil, and about 1-3% soy flour.

7. A method to culture entomogenous nematodes in liquid medium, which comprises providing the medium of claim 1, preinoculating the medium with a bacterial symbiont, inoculating the medium with a culture of entomogenous nematodes, providing a means of agitating and aerating said inoculated medium during the reproductive cycle of the nematode culture, and recovering the infective juveniles.

8. A method to culture entomogenous nematodes in liquid medium, which comprises providing the medium of claim 6, preinoculating the medium with a bacterial symbiont, inoculating the medium with a culture of entomogenous nematodes and providing a means of agitating said inoculated medium during the reproductive cycle of the nematode culture, and recovering the infective juveniles.

9. The method of claim 7 wherein J3 and J4 stage juveniles predominate in the nematode inoculate.

10. The method of claim 7 wherein the nematode is *N. carpocapsae* and the symbiont is *X. nematophilus*.

11. The method of claim 7 wherein second generation infective juveniles are formed within ten to sixteen days after inoculation with a starting population of juveniles.

12. The method of claim 11 wherein second generation infective juveniles are formed within ten days after inoculation with J3 stage juveniles.

13. The method of claim 7 wherein the reproductive rate exceeds 200 per generation.

14. The method of claim 7 wherein the medium is resupplied during the J3 and J4 developmental stage.

15. The medium of claim 1 which has further been inoculated with the juvenile form of said nematodes.

16. The medium of claim 1 wherein the emulsifier is provided by egg yolk, the yeast source is provided by yeast cells, the vegetable oil is corn oil, and the source of protein is soy flour.

* * * * *